United States Patent
Milo

(10) Patent No.: US 8,475,491 B2
(45) Date of Patent: Jul. 2, 2013

(54) SURGICAL STAPLING SYSTEMS

(75) Inventor: Simcha Milo, Haifa (IL)

(73) Assignee: QuickRing Medical Technologies, Ltd., Haifa (IL)

( * ) Notice: Subject to any disclaimer, the term of this patent is extended or adjusted under 35 U.S.C. 154(b) by 150 days.

(21) Appl. No.: 12/907,698

(22) Filed: Oct. 19, 2010

(65) Prior Publication Data

US 2011/0034953 A1 Feb. 10, 2011

Related U.S. Application Data

(63) Continuation of application No. PCT/IB2009/051473, filed on Apr. 7, 2009.

(60) Provisional application No. 61/046,635, filed on Apr. 21, 2008.

(51) Int. Cl.
*A61B 17/08* (2006.01)

(52) U.S. Cl.
USPC .......................................... 606/213; 606/219

(58) Field of Classification Search
USPC ........... 606/75, 139, 151, 153, 155, 219–221, 606/306, 308; 411/457–458, 473, 920–921, 411/923, 444, 442, 446, 475; 227/901, 902; D24/145; 24/466, 474, 476, 485, 572.1, 575.1, 24/578.13
See application file for complete search history.

(56) References Cited

U.S. PATENT DOCUMENTS

| | | | |
|---|---|---|---|
| 4,347,847 A | 9/1982 | Usher | |
| 4,505,273 A | 3/1985 | Braun et al. | |
| 4,887,601 A | 12/1989 | Richards | |
| 5,122,155 A | 6/1992 | Eberbach | |
| 5,147,374 A | 9/1992 | Fernandez | |
| 5,246,443 A * | 9/1993 | Mai ................................ | 606/78 |
| 5,947,999 A * | 9/1999 | Groiso .......................... | 606/219 |
| 6,702,826 B2 | 3/2004 | Liddicoat et al. | |
| 2004/0173659 A1 | 9/2004 | Green et al. | |
| 2004/0236419 A1 | 11/2004 | Milo | |
| 2005/0283190 A1 | 12/2005 | Huitema et al. | |
| 2006/0020336 A1 | 1/2006 | Liddicoat | |
| 2006/0291981 A1 * | 12/2006 | Viola et al. ..................... | 411/457 |
| 2007/0010854 A1 | 1/2007 | Cummins | |
| 2008/0217376 A1 | 9/2008 | Clauson et al. | |
| 2008/0277450 A1 | 11/2008 | Dudai | |

* cited by examiner

*Primary Examiner* — Corrine M McDermott
*Assistant Examiner* — Robert A Lynch
(74) *Attorney, Agent, or Firm* — Fitch, Even, Tabin & Flannery LLP

(57) ABSTRACT

Interengaging surgical staples (11, 31, 51, 71) are provided that are useful in systems for the surgical correction of defects in cardiac valves and/or supporting weaknesses in abdominal regions. The staples are constructed with at least one ring (21, 41, 61, 81) extending laterally from the upper end of one staple leg (15, 35, 55, 75), which once implanted provides for interengagement with the next staple by passage of the other leg (13, 33, 53, 73) of it therethrough. Either shape-memory staple design or an implantation tool causes the two staple legs to curve respectively toward each other once having penetrated the tissue, thus gathering and constricting the tissue in a region below the surface thereof. Elastic sections (67, 83) may be provided in the crown connectors to allow flex in the plane thereof.

11 Claims, 4 Drawing Sheets

SURGICAL STAPLING SYSTEMS

CROSS REFERENCE TO RELATED APPLICATIONS

This application is a continuation of International Application No. PCT/IB2009/051473, filed Apr. 7, 2009, which claims priority from U.S. Provisional Application Ser. No. 61/046,635, filed Apr. 21, 2008, the disclosures of each of which are incorporated herein by reference.

FIELD OF THE INVENTION

This invention relates to stapling systems designed to surgically correct defects in cardiac valves and to provide support in abdominal and other regions of the body. More particularly, it relates to methods and systems for the efficient and effective repair of an incompetent cardiac valve by constructing a continuous encircling ring in situ adjacent the valve from a series of interengaging staples and for the repair of weakness in regions of the abdominal cavity by constructing a similar continuous ring in combination with a supporting mesh sheet.

BACKGROUND OF THE INVENTION

Rheumatic, connective tissue or ischemic heart diseases may heavily affect the configuration of the atrioventricular heart valves. Diseased valves may become narrow, incompetent or both. A great many patients suffering from ischemic heart disease, who previously underwent myocardial infarctions, consequently develop various degrees of mitral valve incompetence. Typically in those patients, the valve may grossly seem to be normal; yet its annulus is dilated, causing coaptation (i.e. interengagement) of the leaflets to be disturbed and resulting in incompetence of the valve. Such patients should benefit from an annuloplasty as a repair.

Annuloplasty rings have now generally become essential components of reconstructive surgery of the mitral and tricuspid valves. Their safety and durability have been proven in numerous clinical studies that have occurred since their genesis in the late 1960's. Subsequent experimental and clinical echocardiographic studies showed that the mitral and tricuspid annuli change continuously in size and shape during the cardiac cycle. Flexible rings were developed that could adapt to such changes. Although such flexible rings may avoid constraining the natural flexibility of the native annulus while still improving valve function, there are some disadvantages in using flexible as well as non-flexible, rigid rings. For example, when the suture spacing along the annulus is not matched to the spacing on the ring, tension in the tissue may result and cause tissue puckering or tearing. Thus, it is not yet proved that flexible rings have to be a complete solution to these problems.

The prevailing techniques that are now used throughout the world, when not resorting to a full valve replacement, generally employ a stabilizing annuloplasty ring for the repair that will likely reduce the circumference of the valve. This is usually accomplished by suturing into place an elastic, semi-rigid or rigid ring that is about equal to or smaller than the circumference of the native annulus being reduced; the ring may have a closed shape or be open, e.g. a C-shape. Installation takes place using regular sutures, in much the same manner as when a full valve replacement is carried out, and the procedure may consume as much time as a full valve replacement, for example, an average of about 25 to 35 minutes. Accordingly, improved annuloplasty systems and methods of reducing this time of surgery have continued to be sought.

More recently, there have been proposals to reduce the circumference of the incompetent valve by placing a series of sutures in the tissue that would gather and constrict the tissue, as shown, for example, in U.S. Pat. No. 5,593,424. There have been other proposals to insert a series of staple-like plication bands in the tissue at the perimeter of the valve, which individual plication bands are interconnected in some manner by linkage constructs, such as a filament or a band which is threaded through a passageway in a bridge region of the plication band, as shown in U.S. Pat. No. 6,702,826. Other proposals would use a series of tethered clips that are individually implanted along the perimeter of the incompetent valve before the tether is manipulated to cinch it within the clips and circumferentially tighten the valve annulus as shown in U.S. Pat. No. 6,986,775. U.S. Pat. No. 7,004,958 proposes inserting shape-memory staples through the wall of the coronary sinus and into the wall of the mitral valve; the staples pierce and gather up the mitral valve annulus tissue to tighten the mitral valve annulus. In U.S. Pat. No. 7,037,334, there is a proposal for a catheter-based annuloplasty through the implantation of a series of local plications which individually gather a portion of the tissue; shape-memory metallic elements that will return to a state which causes tissue located between initially spaced apart legs to be gathered or pinched together in order to constrict an incompetent valve annulus. U.S. Pat. No. 7,485,142 shows the use of a plurality of individual linkers that have anchors for implantation into heart valve tissue which carry upstanding posts having arms to connect with an adjacent post. The arms are formed of shape-memory material and shrink in length to constrict the heart valve tissue.

A hernia is one of the most common ailments of mankind; approximately five percent of the adult male population is affected. Basically, a hernia is a weakness or hole in the abdominal wall through which abdominal contents such as bowels may protrude. The surgical repair of an inguinal hernia, (i.e. inguinal herniorrhaphy) and repair of abdominal wall hernia are among the most common procedures performed, generally on an outpatient basis. Five hundred thousand inguinal herniorrhaphies and about one hundred and eight thousand abdominal herniorrhaphies may be performed each year in the United States. In the case of abdominal wall repair, whether done openly or laparoscopically, the procedure is such that an anesthetic is first administered to the patient, and the surgeon then makes the relevant incisions in the patient's abdominal wall. Supporting abdominal muscles and fascia are dissected to reveal the hernia sac, and the herniated contents protruding through the opening in the abdominal wall are returned to the abdomen. Thereafter, the surgeon closes the hernia sac either primarily or using a supporting artificial mesh implant. The local tissues are then sutured together from opposite sides of the weakened tissue, hole or hernia.

Stretched or otherwise weakened tissue may be cut away, and a patch of artificial material is often sutured or stapled to the normal tissue to replace the stretched or otherwise weakened tissue or to reinforce over the outside or inside of the repair. The incision is then closed over the repair. Recovery time necessary prior to heavy lifting or strenuous labor is usually six to eight weeks. Examples of such repair are seen in U.S. Pat. Nos. 4,347,847 and 5,122,155.

None of the foregoing proposals as practices has yet been considered to provide a completely favorable solution to these problems of incompetent valves and of efficient and satisfactory hernia repair; thus, the search for better solutions has continued.

SUMMARY OF THE INVENTION

It has been found that the implantation of a series of interengaging surgical staples, wherein each one at the time of its implantation interengages with the last implanted staple as a step in creating a ring to totally surround an incompetent valve, provides an efficient and effective method of annuloplasty to cause the valve leaflets to again coapt as desired and avoid regurgitation. Such interengaging staples have a pair of spaced apart legs that are connected at their upper ends through a crown connector of a fixed predetermined length that will reside in juxtaposition with the surface of the tissue once implantation takes place; portions of the legs that are embedded in the tissue bend or curve toward each other, gathering the tissue in a region below the surface to effect the constriction of the perimeter of the valve annulus to shorten same and return the leaflets to effective coaptation and the valve to become competent. Staples with a shock-absorbing crown connector are provided for herniorrhaphy.

In one particular aspect, the invention provides a surgical staple which comprises two spaced apart legs, and a crown connector which joins said legs to each other at upper ends thereof and spaces said legs a predetermined fixed distance apart from each other at their upper ends, said legs having a substantially constant cross section in the region above their lower ends which are pointed, one of said legs being formed with an integral ring extending laterally therefrom in a direction away from said other leg, said ring being oriented perpendicular to said leg and having an aperture proportioned to receive one leg of a similar surgical staple, said staple being designed to allow said two legs to become bent toward each other once said pointed lower ends have penetrated the tissue surface so as to assume a curved configuration and gather tissue below said surface and constrict same.

In another particular aspect, the invention provides a method of implanting surgical staples to form a ring-like arrangement for an annuloplasty operation, which method comprises implanting a first staple having two spaced apart legs and a crown connector which joins said legs to each other at upper ends thereof and spaces said legs a predetermined fixed distance apart from each other at their upper ends, with at least one of said legs being formed with an integral apertured ring extending laterally therefrom in a direction away from said other leg, implanting a second surgical staple, which also has first and second such legs joined by a crown connector that spaces them a predetermined fixed distance apart at their upper ends and has an integral ring extending laterally from said second leg, by passing said first leg through the aperture in the ring of said first implanted staple so as to interengage the two staples, and implanting a plurality of additional staples similar to said second staple with the first leg of each passing through the aperture in the ring of the last implanted staple to create an incomplete or complete ring-like arrangement in the tissue at the perimeter of an atrioventricular valve, said respective legs of each said staple becoming bent toward each other below the surface of the tissue to achieve a curved configuration toward each other and thereby gather tissue below the surface and constrict same.

In a further particular aspect, the invention provides a method of herniorrhaphy performed openly or endoscopically, which method comprises the steps of placing a flexible textile patch on the abdominal region of a patient where weakness has occurred, implanting a first staple having two spaced apart first and second legs and a crown connector which joins said legs to each other at upper ends thereof and spaces said legs a predetermined fixed distance apart from each other at their upper ends so that both legs pass through the textile patch, each of said legs being formed with an integral apertured ring extending laterally therefrom in a direction away from said other leg and said crown connector includes a nonlinear elastic section, implanting a second surgical staple, which also has first and second such legs joined by a crown connector that spaces them a predetermined fixed distance apart at their upper ends by passing said first leg through the aperture in the ring associated with the second leg of said first implanted staple and then through the textile patch so as to interengage the two staples, which staple has an integral ring extending laterally from said second leg and a nonlinear elastic section in its crown connector, and implanting a plurality of additional staples similar to said second staple with the first leg of each passing through the aperture in the ring of the last implanted staple and then through the textile patch to create a ring-like arrangement in the tissue that borders the area of weakness of the patient, said respective legs of each said staple becoming bent toward each other below the surface of the tissue to achieve a curved configuration toward each other and thereby gather tissue below the surface and constrict same.

DETAILED DESCRIPTION OF THE PREFERRED EMBODIMENTS

Figure 2:
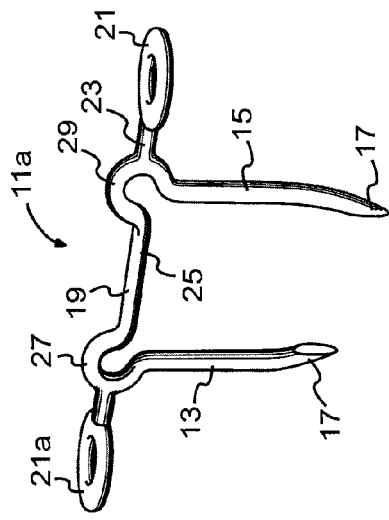
FIG. 2 is a perspective view of a surgical staple similar to that shown in FIG. 1 with an integral ring formed at the top of each leg.

Basically, the invention provides surgical staples of a design that they will both constrict tissue and interconnect with one another, so as to instantly create a chain that can be used to reconfigure a tissue region, particularly at the perimeter of an incompetent atrioventricular valve, or support a region of weakness in a body cavity. In this manner, the series of interengaged staples perform the function of an annuloplasty ring; many forms of such rings have been used for some decades to reconfigure incompetent heart valves. The staples are also useful in combination with a flexible mesh patch in performing a herniorrhaphy. The design of the staples is such that a single delivery step is effective to not only interengage the staple being delivered with that last staple placed, but to, at the same time, effect a precise amount of gathering or constriction of the tissue at a location below the upper surface of the tissue. These surgical staples have, at the time of penetration of the tissue surface, a pair of substantially parallel legs with pointed lower ends that are interconnected at their upper ends by a central connector bar or crown connector which spaces the upper ends of the legs a fixed predetermined distance apart, which distance does not change. By substantially parallel is meant that the legs may be straight or may have a shallow curvature, e.g. the tip may be aligned at an angle up to about 15 degrees toward the opposite leg. In other words, the substantially parallel legs may be parallel or may be either straight or with a shallow curvature and inclined toward each other.

One of the two legs has an integral ring affixed thereto at its upper end. This ring or loop provides an aperture that is proportioned to receive passage of the non-ring-bearing leg of an identical staple to effect the interengagment of two adjacent staples in this manner. When a complete closed ring is constructed, the first staple implanted would carry two such rings in a flanking orientation, and the final staple implanted would be a simple staple to close the ring as each leg is passed through a ring of the first and last staples implanted.

At the time of delivery, the pointed ends of the legs pierce the tissue at spaced apart points determined by the length of the connector bar. Once below the surface of the tissue, the legs are caused to bend or curve toward each other, and in this manner, they gather the tissue in this region below the surface and effect a constriction in a direction defined by the linear connector bar. As explained hereinafter, the movement of the legs toward each other can be either as a result of a shape-memory attribute of the metal from which the surgical staple is fabricated, or a result of the action of the delivery device or tool on the staple itself as it is being delivered and the tips have penetrated the surface of the tissue. Because the remainder of the staple apart from the two legs, resides on or above the tissue surface and does not change in length, all of the contraction occurs below the tissue surface.

The surgical staples are made from a suitable biocompatible, likely metal alloy, material; examples include stainless steel, titanium alloys, Nitinol, other biocompatible nickel-chromium alloys and the like. They may also be made of layered metals where one metal is sandwiched between two others to provide a composite material such as memory and non-memory superelastic alloys and metals. As mentioned above, the staple may be made of standard surgical staple material, e.g. biocompatible metals, such as titanium alloy and clad stainless steels, or of a material having shape-memory characteristics; for example, it may be temperature-dependent Nitinol that will return to a preset shape once the surgical staple warms to body temperature. Alternatively, it may be of a so-called superelastic material, e.g. superelastic Nitinol, or other nickel-titanium alloy or metal alloys. In such instance, the staple is formed and treated to give it a predetermined final set shape to which it will return; then it is deformed without harm to a delivery shape where the two legs are parallel to each other.

In addition to such shape-memory materials, the surgical staples can be made from other biocompatible metals well known in this art that have been used for decades for surgical staple manufacture and which have been found to have a long lifetime in the human body without degradation or cause of undesirable side effects. When such materials are used for fabrication of the surgical staples, then a delivery device is employed which applies forces to the legs at locations below their upper ends to cause the two legs to bend or preferably curve toward each other at locations below the tissue surface so as to securely gather tissue therebetween and create a constriction of a predetermined amount, e.g. 1 or 2 mm in the tissue below its upper surface, in the direction defined by the rigid, fixed connecting bar.

Figure 1:
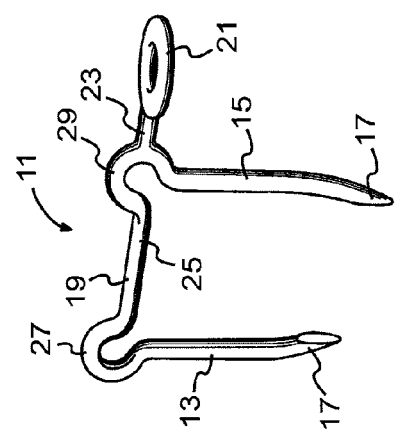
FIG. 1 is a perspective view showing an interengaging staple embodying various features of the invention with its two legs shown generally parallel to each other in the form in which it might be implanted into heart valve tissue.

Illustrated in FIG. 1 is a surgical staple 11 which includes a pair of legs 13, 15 which have pointed bottom ends 17. The legs are interconnected at their upper ends through a crown connector 19. At the upper end of the leg 15, there is a ring 21 that is connected thereto by a short stub arm 23. The ring 21 extends laterally from the leg 15 in a direction directly away from the leg 13. The connector 19 includes a central linear bar 25 that is flanked by a pair of ears 27, 29. The ears are loop sections of about 270 degrees each that may be considered to constitute parts of both the connector 19 and the legs 13, 15.

A staple blank might be laser cut from a flat sheet of a biocompatible metal alloy, and the ring 21 is then twisted 90°. Following edge removal and polishing of the laser-cut blank, the staple has the rounded appearance seen in FIGS. 1, 2 and 3; i.e. it has a substantially constant circular cross section, except for the pointed ends 17. Both the ring 21 and the ear 27 are proportioned to have a central aperture that is larger in diameter than the circular cross-section of the leg 13 (and the ring 21), so that such can be respectively received therewithin. The aperture may be as small as only about 20% greater, but might be about 4 times the size. Generally, it will not be more than about twice the size. In the surgical staple 11 illustrated in the FIG. 1, the ring or loop 21 is aligned so that it lies transverse to the leg 15 to which it is attached; it preferably lies in a plane that is substantially perpendicular to a plane wherein the legs 13,15 lie. Its location at the upper end of the leg 15 is preferably such that it is co-planar with the plane in which the linear bar central portion 25 of the crown connector lies. As a result of such alignment, when such surgical staples are inserted or implanted in tissue, both the bar 25 and the ring 21 will lie juxtaposed with the surface of the tissue into which the implantation occurs. The symmetrical ears 27, 29 are also positioned so that the apertures therewithin would similarly lie within this plane; thus, the ear 27 would receive and accommodate a portion of the ring 21 of the last-implanted staple through which the leg 13 would be passed.

Figure 3:
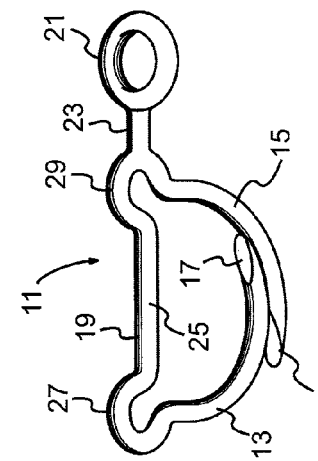
FIG. 3 is a perspective view of the surgical staple shown in FIG. 1 taken from a different angle with its two legs juxtaposed in final implanted position.

When the surgical staple 11 is fabricated from shape-memory material, it might be laser cut from a flat sheet of biocompatible metal alloy, subjected to chemical, mechanical or electrical surface treatments to polish it, and then suitably treated to endow the staple with shape-memory characteristics so it would revert to the shape shown in FIG. 3. It would then be bent to the shape illustrated in FIG. 1 and loaded into a delivery tool. The delivery tool, operated by a cardiac surgeon, would be used to simply implant each staple with the leg 13 passing through the ring 21 of the last implanted staple so that the linear bar 25 and the ring 21 of this staple would be juxtaposed against the upper surface of the tissue, with a section of the adjacent staple ring 21 being received in the ear 27. During normal operation, the staples 11 might be, for example, sized to create a constriction of about 2 mm in the tissue below the surface wherein implantation occurs. As mentioned above, the crown connector 19, which includes the linear bar 25 and the two ears 27, would be designed to be of a fixed dimension so that only the regions of the legs lying below their interconnections with the lower ends of the ears 27, 29 would bend or curve toward each other to effect the gathering of the tissue. It is in this fashion that the constriction is relegated to regions within the tissue itself, spaced below its surface. As a result, it creates a more uniform contraction or gathering of the tissue and avoids any propensity to tear at the surface.

When shape-memory staples are not used, the staples, which are made out of biocompatible metal alloys, are then implanted using a stapling tool that will effect a curvature to the legs so that they will assume the arcuate shapes shown in FIG. 3. As a result, it can be seen that the lower major portions of the legs 13 and 15 bend toward each other in arcuate shape from the uppermost remaining straight sections and in doing so constrict the tissue in regions below the surface, thus accomplishing the reshaping desired when reconfiguring a faulty atrioventricular valve.

Figure 4:
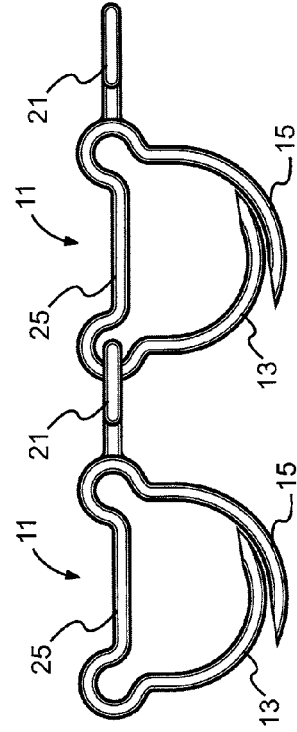
FIG. 4 is a front view showing two surgical staples of the type illustrated in FIG. 1 in interengaging orientation with their legs juxtaposed.

FIG. 4 depicts two such interengaged staples 11 as the staples would be employed to create a partial or complete ring about a valve annulus, for example, that of an incompetent mitral valve. Although in some instances only a partial ring might be employed, it has been found that improvement in an incompetent valve often might be only temporary if the annuloplasty were limited to less than 360 degrees about the perimeter. Oftentimes, it has been found that the heart valve tissue, when only constricted by a partial ring annuloplasty, may well stretch in other locations, such as the intertrigonal region; as a result, incompetence may return to some degree. In FIG. 4, it can be seen that the individual legs 13 and 15 are shown as having curved from their substantially parallel orientations at the time of delivery (shown in FIG. 1) to now lie juxtaposed with each other. As a result, they would have gathered and constricted the heart valve tissue in the region encompassed by the two legs below the linear bar section 25.

When a complete annuloplasty ring is to be created as the end result of this multiple staple annuloplasty system, the first staple or element placed should be one having a pair of such rings. Depicted in FIG. 2 is such a staple 11a which has a second ring 21a extending laterally from the upper end of the leg 13 in the region of the ear 27. Both rings lie in a plane perpendicular to the legs 13,15 which plane includes the linear bar 25. Thus, in reconfiguring an incompetent atrioventricular valve using the surgical staples 11 to create a complete ring about its perimeter, a staple 11a is first implanted is having a pair of rings 21,21a. If it is one formed of a shape-memory material, its elastic properties allow it to be distended to a shape with its legs in substantially parallel orientation shown in FIG. 2, in which form it would be delivered into the upper surface of tissue, i.e. a valve annulus to be reconfigured. Because of the shape-memory characteristics, the legs 11,13 would then revert from their parallel, distended orientations to curve toward each other. Such closing movement would continue until the legs 11,13 became juxtaposed as shown in FIG. 3 in closed orientation, thereby constricting the tissue therebetween in a region below the surface. As the surgeon builds the annuloplasty system encircling the valve being reconfigured, he would begin at one of the two rings 21,21a and implant staples 11 one by one, by passing the leg 13 of each staple through the aperture in the ring 21 of the last implanted staple to create the encircling arrangement. The surgeon gauges the placements such that, when the circle of surgical staples is nearly closed, the gap remaining between the last staple 11 implanted and the double-ringed staple 11a first implanted is such that the two open rings 21,21a are spaced apart the approximate distance of the pair of straight legs 13, 15 of a single staple. The gap is then closed using a single simple staple; it may be one resembling that shown in FIG. 1 with the ring 21 and its connecting arm 23 simply omitted.

Figure 5:
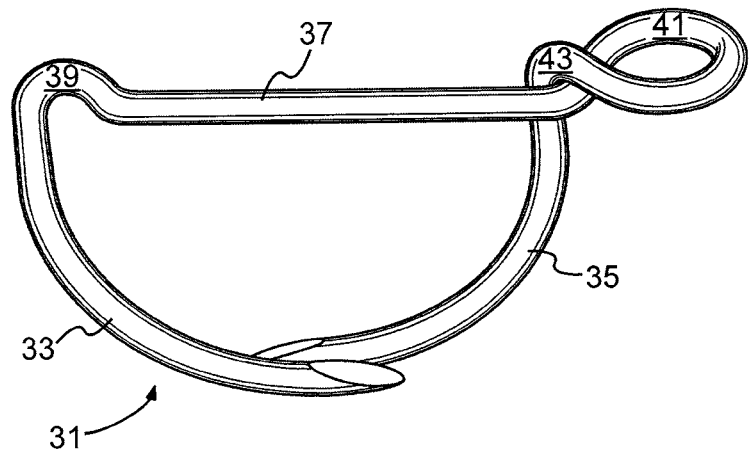
FIG. 5 is a view similar to FIG. 3 of an alternative embodiment of a surgical staple embodying various features of the invention formed of wire.
Figure 6:
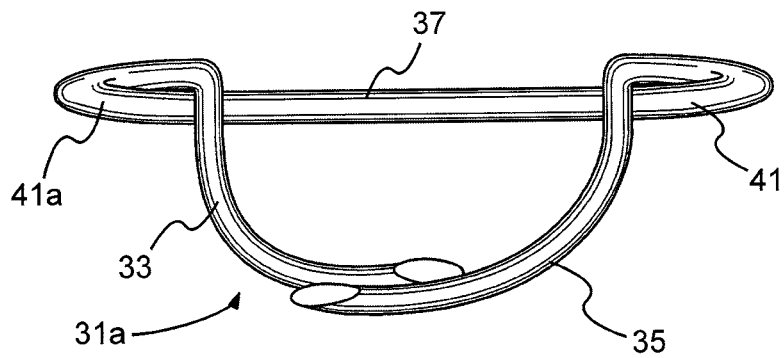
FIG. 6 is a perspective view of an alternative embodiment of a surgical staple similar to that shown in FIG. 5 but having two integral rings.

Shown in FIG. 5 is an alternative embodiment of a surgical staple 31, which is shown in a constricted orientation as in FIG. 3; the staple 31 likewise incorporates a pair of legs 33, 35 with a linear crown connector 37 at the upper ends thereof. Its construction allows formation of the staple 31 by bending a metal alloy wire of circular cross section to provide a wire-form surgical staple. Other cross-section shaped wires might be used, e.g. a layered metal wire of generally square or wire of non-round cross-section. The wire is shaped such that a similar ear 39 is formed at the upper end of the leg 33; however, the symmetrical ear is omitted. A transversely oriented ring 41 is provided by forming a loop from the wire at the opposite end of the connector 37 at the top of the leg 35 and then twisting the wire for 270°, creating a twist-bend 43. The result is such that the looped wire forms a 360 degree ring 41 attached at the twisted joint 43. The transverse ring 41 is again oriented so as to lie in substantially the same plane as the linear connector 37, both of which would lie juxtaposed with the upper surface of the tissue in the implanted annuloplasty system. Again, the ear 39 would extend above the surface of the tissue and accommodate the pertinent portion of the ring 41 of the last-implanted staple in its central aperture or bight. To form a complete ring around an incompetent valve, the first staple implanted would have 2 rings 41,41a as the staple 31a shown in FIG. 6.

Figure 7:
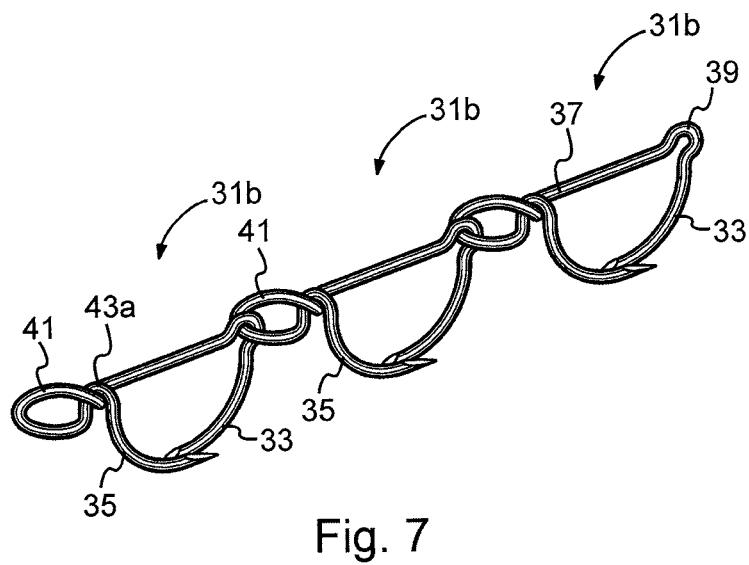
FIG. 7 is a perspective view showing three surgical staples generally similar to those of FIG. 5, interengaged with one another in a chain.

Three such generally similar staples 31b are illustrated in FIG. 7 where they are shown as a part of a chain. The only difference is that, in the staples 31b, the loop 41 is twisted 450° to create a more pronounced twisted joint 43a. Once implanted, the undersurface of the ring 41 and that of the linear connector 37 would be juxtaposed with the surface of the tissue into which the surgical staple is delivered, similar to the staples 11.

It should be apparent from the foregoing that this annuloplasty system provides the surgeon a way to reconfigure an incompetent valve quickly, using simply a loaded delivery tool which will serially deliver individual staples to create an encircling arrangement about the valve that will effect such reconfiguration that the valve leaflets again coapt as desired and intended. The surgeon need not individually crimp staples or other plication bands that have been earlier implanted in the tissue, but can quickly simply deliver surgical staples, one after another, simply passing one leg of each staple through the aperture provided by an integral, transverse ring affixed to the upper end of one leg of the last implanted staple. As a result, the annuloplasty system gives rise to ease, speed and accuracy of operation and allows the surgeon to achieve valve reconfiguration as desired.

Hernias generally erupt when a weakened location in the abdominal wall stretches and/or tears, which may permit organs inside to pouch outward, often looking like a balloon beneath the skin. Another type of hernia evolves as a result of incomplete healing and scaring of an abdominal wall incision, following an intra-abdominal operation; it is termed an "incisional hernia". Certain of these hernia types are often corrected by an additional procedure which reinforces the tissues by suturing a flexible surgical mesh material to the abdominal wall or the like. A kit comprising a multiple number of the staples 11 or 31 and flexible mesh, synthetic fiber textile material or the like may be used to repair a hernia, but staples of alternative shapes that incorporate not only the interlocking feature but also a so-called shock-absorbing feature can be advantageously employed. These alternative staples are likewise used to constrict the body tissue below the surface between two leg entry points that are spaced apart a finite distance as set by each crown connector as described above. However, the crown connectors are shaped to allow a potential increase in intra-abdominal pressure to be divided more evenly throughout the entire circumference of the created ring rather than being concentrated in the vicinity of a single staple or a weak location where, with time, dislodging or tearing may often occur Such an arrangement which provides some flexing or elastic movement in the chain of staples should better accommodate the occurrence of such momentary rises in abdominal pressure and thereby reduce the recurrence rate of herniorrhaphy procedures, which is currently significantly high.

Figure 8:
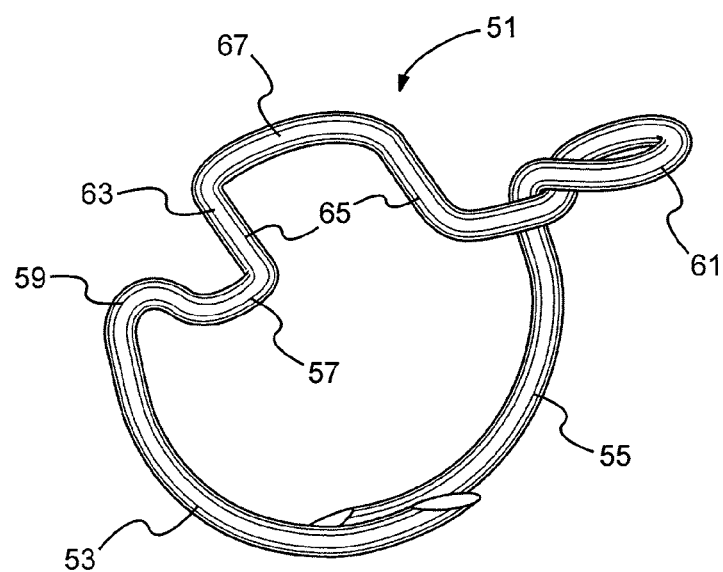
FIG. 8 is a perspective view of an alternative embodiment of a surgical staple, somewhat similar to that shown in FIG. 5 wherein the crown connector is formed with a "U" shape, springlike elastic section.

FIG. 8 shows one embodiment of such a shock-absorbing staple 51. It resembles the staple 31 in that it includes two legs 53,55 which are spaced apart by a crown connector 57 with an ear 59 formed atop the leg 53 and a ring 61 formed atop the leg 55. However, instead of the crown connector 57 being formed with a straight linear section 37, it is formed with a major U-shaped bend 63 having a pair of arms 65 interconnected by an arcuate link 67. The staples 51 would be implanted into abdominal tissue or the like by protrusion through a reinforcing flexible mesh material patch 69 in the manner schematically shown in FIG. 9. The mesh material patch 69 would have a sufficiently large area to cover the weakness in the abdominal cavity, but likely would not be as oversize as schematically shown; it would usually be tailored by the surgeon by trimming prior to implantation to be about 3-4 cm greater than the defect. With any organs moved back into place by repairing muscle damage, the flexible mesh material patch 69 is secured in contact with the surface of the tissue covering the cavity by creating an encircling ring of staples 51 that borders the region of hernia defect.

The orientation of each staple 51 in the encircling ring is such that a U-shape bend 63 lies radially outward of the circle defined by the legs 53,55 of the plurality of staples. As a result, when the occurrence of intra-abdominal pressure stresses the tissue, the legs 53,55 of the plurality of staples can elastically spread-apart as a result of some slight opening of the radius of the arcuate link 67 and bending of the arms 63.

Figure 10:
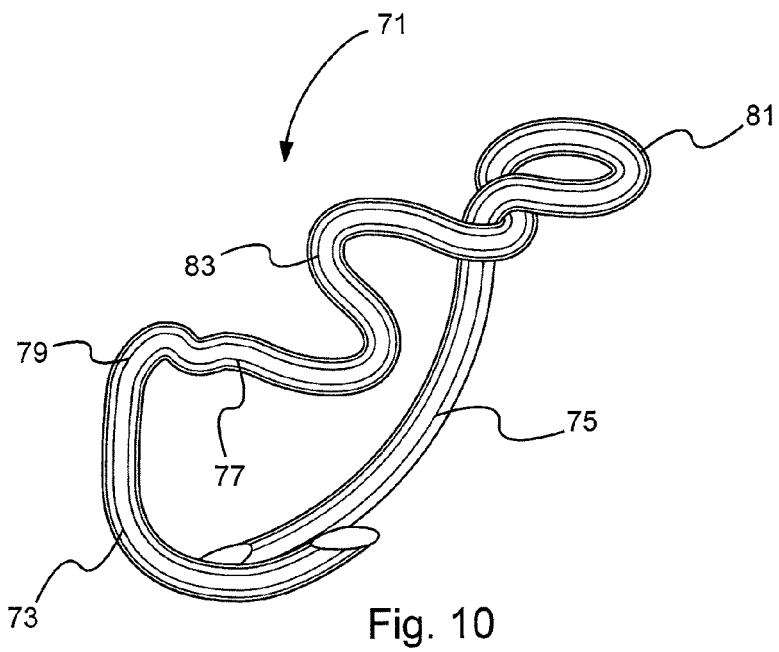
FIG. 10 is a perspective view similar to FIG. 8 showing another alternative embodiment of a staple having an "S" shape, springlike elastic section in its crown connector.

Shown in FIG. 10 is an alternative embodiment of such a shock-absorbing staple 71 which likewise has a pair of legs 73,75 spaced apart a predetermined distance by a crown connector 77; it includes an ear 79 atop the leg 73 and a transverse ring 81 atop the leg 75. The ability to momentarily flex and then return to the predetermined original shape is provided by an S-shaped section 83 in the form of 3 legs, oriented transverse to a line drawn between the ear 79 and the ring 81, interconnected by arcuate bends, that forms the major portion of the crown connector 77 and provides the desired springiness. Illustrated in FIG. 11 are a multitude of the staples 71 implanted through a patch of the surgical reinforcing flexible mesh material 69 so as to encircle a weakened region of an abdominal cavity.

Such flexible mesh patches 69 can be woven or knitted or made of other suitable fabric material of the type that has long been used in hernia repair. Preferably, patches are made of polymeric material that is biocompatible, such as polypropylene or polytetrafluoroethylene (PTFE). Standard surgical stapling has heretofore been used as well as suturing for hernia repair. Endoscopic staplers are commercially available to facilitate endoscopic hernia repair, such as the ENDOPATHY ES endoscope which is marketed by the Ethicon division of J&J. Staplers of this general type can be adapted to implant either the staples 51 or the staples 71; the design may be such to implant either shape-memory staples or staples made of standard metal alloys or layered metals which will retain the shape established by the stapling tool, subject of course to the elastic region of the crown connectors.

Figure 9:
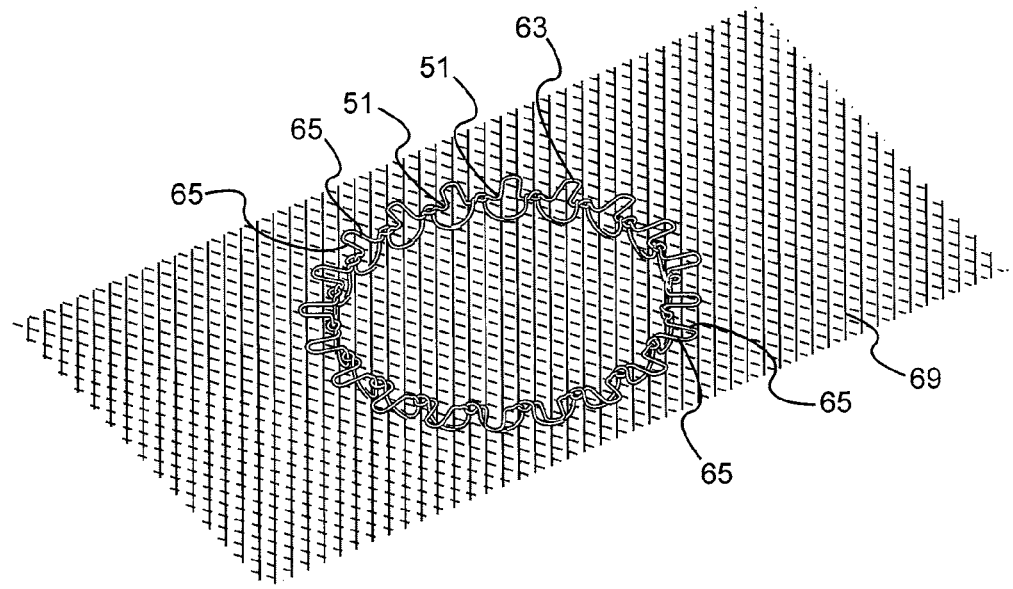
FIG. 9 is a perspective view schematically illustrating how a plurality of staples such as that shown in FIG. 8 can be implanted through a textile patch in a herniorrhaphy.

The flexible polymeric mesh material, while providing reinforcing support against movement in a direction transverse to plane thereof (so as to thereby support the weakened abdominal region or the like from bulging outward), allows some inherent stretching movement in the plane thereof. The encircling chain of interlocking staples 51 or 71, as shown in FIGS. 9 and 11, creates a perimeter of finite length and thus provide added support. However, on occasions when momentary rises in interabdominal pressure occur, it is advantageous to accommodate such rises for the comfort of the patient. This end is achieved through the staple construction which provides an elastic, i.e. spring-like or shock-absorbing, section in the crown connector that joins the respective two legs of the staples. By choosing a construction material for the staples that will retain the primary shape of the two curved leg portions that are embedded in the body tissue, but which has a modulus of elasticity within a fairly narrow range; the staples remain securely implanted while the U- or S-shaped section will flex in response to the exertion of force on the implanted, interconnected staples. The arrangement is such that a momentary interabdominal pressure rise results in forces which are distributed throughout the entire ring so that it spreads and then returns to its original shape upon relaxation of such pressure thereby avoiding potential tearing of the repair. Staples might be made of a metal alloy wire or may be laser cut from metal sheets of appropriate thickness and treated to provide them with the desired configuration; for example, stainless steel 316L staples having a cross sectional diameter of about 0.5 to 1.2 mm and a modulus of elasticity of about 193 GPa (giga Pascal) should exhibit the desired springiness. As another example, staples 51 may be made from cobalt-nickel-chromium alloy No. L605 having a diameter of about 0.6-1.2 mm and a modulus of elasticity of about 206 GPa. A target range for modulus of elasticity for such staples might be between about 190 and about 210 GPa. Alternatively, they may be made from medical-grade Nitinol wire of about 0.8-1.2 mm diameter having shape-memory characteristics.

Figure 11:
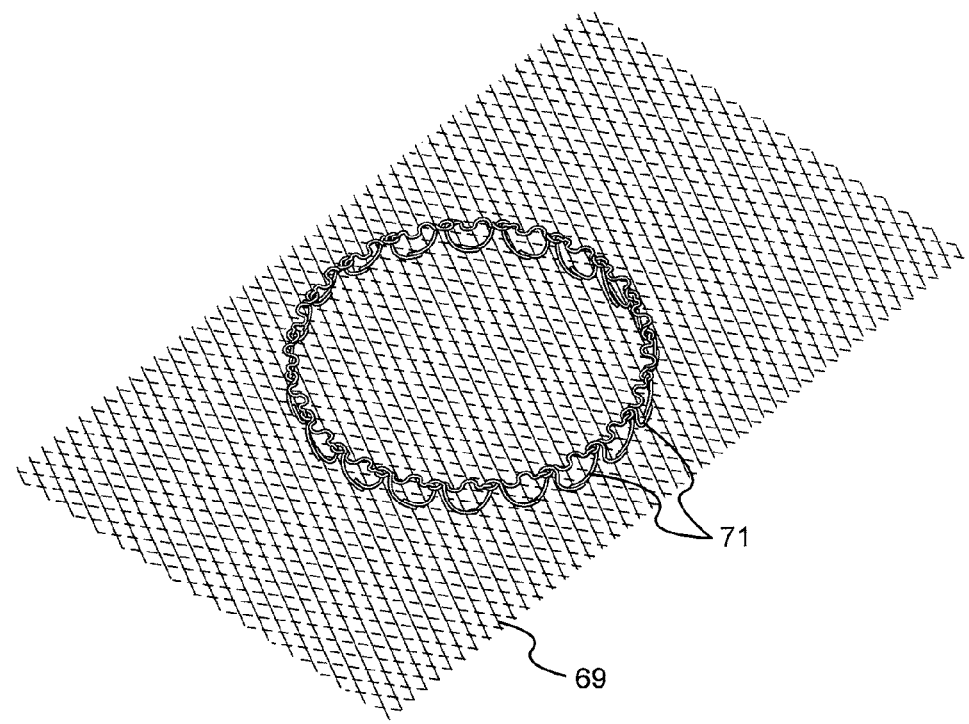
FIG. 11 is a view similar to FIG. 9 showing a plurality of the staples shown in FIG. 10 being used in a herniorrhaphy.

Although not specifically illustrated, it should be understood that in order to provide encircling arrangements of staples such as shown in FIGS. 9 and 11, a kit would be provided that will include (a) multiple staples of the shape shown in FIG. 8 or 10, (b) one such staple having two rings, one at the upper end of each of the legs, (c) one staple without a transverse ring at the upper end of either leg, and (d) a patch of flexible surgical reinforcing fabric.

Although the invention has been described with regard to certain preferred embodiments which constitute the best mode presently known for carrying out the invention, it should be understood that various changes and modifications as would be obvious to one having ordinary skill in this art may be made without departing from the scope of the invention, which is set forth in the claims appended hereto. For example, as mentioned before, although the description has often mentioned the use of shape-memory staples, it should be understood that standard biocompatible metal alloys or layered metals may be used in combination with a delivery tool that would effect the bending of the legs toward each other as a part of the delivery action after the pointed tips of those legs have passed below the surface of the tissue.

Although the use of the central connector having a U-shape bend and an S-shape bend were described, other such non-straight-line shapes may be used to provide precise spacing between the upper ends of the legs when desired to allow some limited flex in the plane of the ultimate ring created by the crown connectors which permit some slight spreading of the implanted legs to follow the physiological movement of the tissue, creating what might be referred to as a "breathing ring".

Particular features of the invention are emphasized in the claims which follow.

The invention claimed is:

1. A plurality of surgical staples for implantation into tissue as a chain, each of which staples comprises
   only two spaced apart legs, and
   a crown connector which joins said two legs to each other at upper ends thereof and spaces said two legs a predetermined fixed distance apart from each other at their upper ends,
   said legs having a substantially constant cross section in the region above their lower ends which are pointed,
   only one of said legs being formed with an integral ring extending laterally therefrom in a direction away from said other leg, said ring being oriented perpendicular to said leg and having an aperture proportioned to receive one leg of a similar surgical staple,
   said staple being designed to allow said two legs to become bent toward each other once said pointed lower ends have penetrated the tissue surface so as to assume a curved configuration and gather tissue below said surface and constrict same as a part of a chain comprising a plurality of pairs of said staples wherein each said staple is a part of a pair wherein one of said only two legs of one staple of the pair resides in said ring aperture of the other staple of the pair.

2. The surgical staples of said plurality according to claim 1 wherein said integral ring has a circular aperture.

3. The surgical staples according to claim 2 wherein said aperture has a diameter at least about 20% greater than the maximum cross sectional dimension of said other leg.

4. The surgical staples of said plurality according to claim 1 wherein said ring is aligned so as to be substantially planar with said crown connector.

5. The surgical staples of said plurality according to claim 1 which is made of a shape-memory material which is so treated that said two legs are substantially parallel and bend toward each other in curved configuration once implanted into a tissue surface, gathering tissue below said surface and constricting same.

6. The surgical staples of said plurality according to claim 1 which is made of a non-shape-memory material and is designed to facilitate said two legs being bent toward each other in curved configuration during the course of their penetration into a tissue surface, thereby gathering tissue below said surface and constricting same.

7. The surgical staples of said plurality according to claim 1 wherein said crown connector includes a nonlinear elastic section.

8. The surgical staples according to claim 7 wherein said crown connector includes a U-shaped section or an S-shaped section.

9. A hernia repair kit which includes a plurality of surgical staples according to claim 8 and a flexible textile patch of mesh material of a size sufficient to cover a weakened anatomical portion of a patient and provide a border thereabout through which said staples can be implanted.

10. The kit according to claim 9 wherein said patch is formed of material woven from inextensible strands of polymer and said kit includes one staple that has a ring extending laterally from each of its only two legs in opposite directions to each other.

11. A hernia repair kit which includes a plurality of surgical staples according to claim 8 and a flexible textile patch of mesh material of a size sufficient to cover a weakened anatomical portion of a patient and provide a border about said weakened portion, through which textile patch said staples can be implanted, wherein said staples are formed of a material having a modulus of elasticity such that said U-shaped or S-shaped section will flex when subjected to momentary rises in inter-abdominal pressure in the human patient.

* * * * *